(12) United States Patent
Severson (10) Patent No.: US 9,713,444 B2
(45) Date of Patent: Jul. 25, 2017

(54) HUMAN-DIGITAL MEDIA INTERACTION TRACKING

(75) Inventor: Joan Severson, Cedar Rapids, IA (US)

(73) Assignee: DIGITAL ARTEFACTS, LLC, Iowa City, IA (US)

(*) Notice: Subject to any disclaimer, the term of this patent is extended or adjusted under 35 U.S.C. 154(b) by 1664 days.

(21) Appl. No.: 12/343,305

(22) Filed: Dec. 23, 2008

(65) Prior Publication Data
US 2010/0076274 A1    Mar. 25, 2010

Related U.S. Application Data (60) Provisional application No. 61/194,101, filed on Sep. 23, 2008.

(51) Int. Cl.
| | |
|---|---|
| A61B 5/16 | (2006.01) |
| G09B 19/00 | (2006.01) |
| G09B 19/22 | (2006.01) |
| G06F 17/30 | (2006.01) |
| G06Q 10/00 | (2012.01) |
| G06Q 50/24 | (2012.01) |

(52) U.S. Cl.
CPC ............ *A61B 5/165* (2013.01); *A61B 5/16* (2013.01); *G06F 17/30029* (2013.01); *G06Q 10/00* (2013.01); *G06Q 50/24* (2013.01); *G09B 19/22* (2013.01)

(58) Field of Classification Search
None
See application file for complete search history.

(56) References Cited

U.S. PATENT DOCUMENTS

| | | | | |
|---|---|---|---|---|
| 5,309,923 A | * | 5/1994 | Leuchter ............. | A61B 5/4088 600/544 |
| 5,377,100 A | * | 12/1994 | Pope et al. .......... | A61B 5/0476 341/20 |
| 5,678,571 A | * | 10/1997 | Brown ................. | A63F 13/005 128/898 |
| 5,724,987 A | * | 3/1998 | Gevins et al. ....... | A61B 5/0484 434/258 |
| 5,899,855 A | * | 5/1999 | Brown ........................ | 600/301 |
| 5,907,831 A | * | 5/1999 | Lotvin et al. ............. | 705/14.27 |

(Continued)

OTHER PUBLICATIONS

Jimison et al., Embedded Assessment of Cognitive Performance with Elders' Use of Computer Games in a Residential Environment, Proceedings of the Workshop on the Cognitive Science of Games and Gaming, Vancouver, British Columbia, Canada, Jul. 26, 2006.*

(Continued)

*Primary Examiner* — William Thomson
*Assistant Examiner* — Manolis Pahakis
(74) *Attorney, Agent, or Firm* — K&L Gates LLP (57) ABSTRACT

A system for human-digital media interaction tracking. One example system includes a database that stores information regarding a user's activity history for various different cognitive tasks, and a computing device that receives user behavior information indicating usage by a user of an interactive software program, the interactive software program associated with at least one of the cognitive tasks. The computing device, in response to the receipt of user behavior information indicating usage by the user of the interactive software program, updates the database information regarding the user's activity history for the at least one of the cognitive tasks.

7 Claims, 8 Drawing Sheets

(56) References Cited

U.S. PATENT DOCUMENTS

| | | | | |
|---|---|---|---|---|
| 5,911,581 | A * | 6/1999 | Reynolds et al. | 434/236 |
| 5,913,310 | A * | 6/1999 | Brown | 128/897 |
| 6,019,607 | A * | 2/2000 | Jenkins et al. | G09B 19/04 434/116 |
| 6,149,441 | A * | 11/2000 | Pellegrino et al. | 434/350 |
| 6,159,014 | A * | 12/2000 | Jenkins et al. | G09B 19/06 273/273 |
| 6,206,702 | B1 * | 3/2001 | Hayden et al. | A61B 5/4076 434/236 |
| 6,231,344 | B1 * | 5/2001 | Merzenich et al. | A61B 5/16 434/236 |
| 6,261,101 | B1 * | 7/2001 | Benitz et al. | G09B 19/06 434/156 |
| 6,280,198 | B1 * | 8/2001 | Calhoun et al. | 434/236 |
| 6,334,778 | B1 * | 1/2002 | Brown | 434/258 |
| 6,409,513 | B1 * | 6/2002 | Kawamura et al. | G09B 17/04 434/178 |
| 6,434,419 | B1 * | 8/2002 | Gevins | A61B 5/0484 600/544 |
| 6,599,129 | B2 * | 7/2003 | Jenkins et al. | G09B 5/04 434/167 |
| 6,632,174 | B1 * | 10/2003 | Breznitz | 600/300 |
| 6,856,913 | B1 * | 2/2005 | Silberstein | 702/19 |
| 7,390,191 | B2 * | 6/2008 | Berman | 434/323 |
| 7,677,896 | B1 * | 3/2010 | Sonwalkar | 434/236 |
| 7,720,784 | B1 * | 5/2010 | Froloff | A61B 5/165 600/300 |
| 7,933,852 | B2 * | 4/2011 | Jenkins | G09B 5/02 706/45 |
| 8,327,395 | B2 * | 12/2012 | Lee | G06Q 30/02 725/10 |
| 9,498,704 | B1 * | 11/2016 | Cohen | G09B 5/00 |
| 2003/0207237 | A1 * | 11/2003 | Glezerman | G09B 5/06 434/118 |
| 2004/0043373 | A1 * | 3/2004 | Kaiserman | 434/350 |
| 2005/0143175 | A1 * | 6/2005 | Ahlquist | A63F 13/10 463/42 |
| 2005/0159921 | A1 | 7/2005 | Louviere et al. | |
| 2005/0187436 | A1 * | 8/2005 | Doniger et al. | 600/300 |
| 2005/0216243 | A1 * | 9/2005 | Graham et al. | G06F 19/3437 703/11 |
| 2005/0283053 | A1 * | 12/2005 | deCharms | 600/300 |
| 2006/0184058 | A1 * | 8/2006 | Silberstein | 600/544 |
| 2006/0184494 | A1 * | 8/2006 | Klingberg | G09B 7/06 706/47 |
| 2006/0286538 | A1 * | 12/2006 | Scalone et al. | 434/350 |
| 2007/0065789 | A1 * | 3/2007 | Goldman | G09B 7/08 434/236 |
| 2007/0065795 | A1 * | 3/2007 | Erickson et al. | 434/307 R |
| 2007/0166675 | A1 * | 7/2007 | Atkins | G09B 5/06 434/236 |
| 2007/0184427 | A1 * | 8/2007 | Packard et al. | 434/350 |
| 2007/0218440 | A1 * | 9/2007 | Delahunt | G09B 23/28 434/236 |
| 2007/0293732 | A1 * | 12/2007 | Delahunt | G09B 7/02 600/300 |
| 2007/0298401 | A1 * | 12/2007 | Mohanty et al. | 434/350 |
| 2008/0003553 | A1 * | 1/2008 | Stark | G09B 5/00 434/236 |
| 2008/0138777 | A1 * | 6/2008 | Rapoza | G09B 19/00 434/238 |
| 2008/0243005 | A1 * | 10/2008 | Jung et al. | 600/481 |
| 2008/0287821 | A1 * | 11/2008 | Jung et al. | 600/544 |
| 2009/0005653 | A1 * | 1/2009 | Jung et al. | 600/300 |
| 2009/0018407 | A1 * | 1/2009 | Jung et al. | 600/301 |
| 2009/0069707 | A1 * | 3/2009 | Sandford | A61B 5/165 600/545 |
| 2011/0119129 | A1 * | 5/2011 | Pradeep | G06Q 30/02 705/14.49 |
| 2011/0137727 | A1 * | 6/2011 | Chung | G06F 3/0346 705/14.55 |
| 2011/0238685 | A1 * | 9/2011 | Garcia Molina | A61B 5/0476 707/769 |

OTHER PUBLICATIONS

Jimison et al., Home-Based Cognitive Monitoring Using Embedded Measures of Verbal Fluency in a Computer Word Game, 30th Annual International IEEE EMBS Conference Vancouver, British Columbia, Canada, Aug. 20-24, 2008.*
Takahasi Dean, Vivity Labs launches Fit Brains brain-training game site, Mar. 19, 2008, from http://venturebeat.com/2008/03/19/vivity-labs-launches-fit-brains-brain-training-game-site/.*
Jimison et al., A framework for cognitive monitoring using computer game interactions, Studies in health technology and informatics—Feb. 2007.*
Green, C.S. et al., "Action Video Game Modifies Visual Selective Attention", Nature, vol. 423, May 2003, pp. 534-537.
Draganski B. et al. "Changes in grey matter induced by training" Nature, vol. 427, Jan. 2004, pp. 311-312.
International Search Report and Written Opinion for International Patent Application No. PCT/US2009/057664 dated Nov. 6, 2009.

* cited by examiner

| | | |
|---|---|---|
| User | First User | |
| Title | Dr. Memory | |
| | Device | Personal Computer |
| | Input | Keyboard, Mouse |
| | Date | 1/5/2009 |
| | Start Time | 4:35:05 pm |
| | End Time | 7:00:06 pm |
| | Total Time of Interaction | 2:35:01 |
| | Rounds Played | 4 |
| | Score: Round 1 | 400 |
| | Score: Round 2 | 570 |
| | Score: Round 3 | 1240 |
| | Score: Round 4 | 1100 |
| | Device | Mobile Phone |
| | Input | Keypad |
| | Date | 1/7/2009 |
| | Start Time | 12:21:35 pm |
| | End Time | 12:53:00 pm |
| | Total Time of Interaction | 21:25 |
| | Rounds Played | 1 |
| | Score: Round 1 | 1150 |
| | Cumulative Time | 2:56:26 |
| | Average Score | 892 |
| | Cognitive Task | Short-term Memory |
| Title | Text Messaging | |
| | Device | Mobile Phone |
| | Input | Keypad |
| | Date | 1/3/2009 |
| | Start Time | 2:39:05 pm |
| | End Time | 2:42:06 pm |
| | Total Time of Interaction | 3:01 |
| | Words Typed | 48 |
| | Cognitive Tasks | Motor Function, Language Processing |

HUMAN-DIGITAL MEDIA INTERACTION TRACKING

CROSS-REFERENCE AND PRIORITY CLAIM

This application is a non-provisional application claiming priority under 35 U.S.C. §119(e) from U.S. Provisional Application No. 61/194,101, entitled "Method and system for tracking, analyzing, timing, and reporting areas of the brain stimulated by digital media," filed Sep. 23, 2008, the entirety of which is herein incorporated by reference.

BACKGROUND

Digital media, including interactive software and accompanying hardware, has become the preferred form of communication and entertainment for many people. People log in, make phone calls, and interact with digitally-based media on a daily basis. Digital media has become the dominant mode by which people seek entertainment, communicate and gain information about the world. Many people choose to read materials hosted online instead of paper-based documents like newspapers and book. E-mail has become more popular than the postal service for letter-writing. Cell phones have replaced the ground-line phone as the preferred means of quick communication. Video games have become a mainstream entertainment medium, expanding beyond the demographic of children and young adults. So called "casual" video games, often available on mobile phones or free on the Internet, are used extensively by an older demographic of users than traditional video games. Digital video and music, which are seemingly passive experiences, are delivered and consumed via on-demand digital access and distribution.

The human brain and mind evolves and adapts to the experiences and environment in which it is exposed. Neuroplasticity and neurogenesis demonstrate that the evolution of the human brain continues throughout an individual's life. Exposure to and use of the different types of digital media stimulates brain function in many ways, regardless of the intentions of the makers of digital media. Specific cognitive tasks, traits and functions are processed in localized regions of the brain, which may be stimulated by interaction with digital media. For example "Surfing the web" or "texting friends" requires cognitive work, and may stimulate areas of the brain required to perform the cognitive tasks associated with executive function, language processing, fine motor skills, and working memory. Another example of cognitive work performed while interacting with digital media is playing video games. Research shows that video games affect certain brain processes and may improve cognitive development (Green, C. Shawn & Daphne Bavelier, Action Video Game Modifies Visual Selective Attention. NATURE May 29, 2003; 423:534-7.) If video games stimulate certain aspects of the brain because of the cognitive functions required for playing them, then it could be inferred that other digital mediums would also stimulate brain processes.

While digital media is becoming a growing part of individuals' lives, there is no comprehensive tracking of individuals' interactions with digital media and mapping of the effects of using digital media on individuals' brains and behaviors. Currently, there are products that track the usage of specific forms of digital media. For example, there are products that track how much a particular website is used, and use this to help websites advertise. Cell phone companies also track the usage of cell phones by subjects for pricing purposes. None of these existing products measure and analyze the potential effects of using these types of digital media on an individuals' cognitive function and development. Additionally, these products do not evaluate the behavioral implications of digital media usage.

Recent research by neuroscientists has suggested the possibility of improving cognition through external stimulus. Called "neuroplasticity," neuroscientists have determined that the brain acts like a muscle, and cognitive "exercise" can stimulate cognitive improvement. Research shows that external stimulus such as physical exercise or interaction with digital media can stimulate brain activity in areas of the brain associated with cognition and improve cognitive development even after the brain stops developing due to age. (Draganski B et al. Neuroplasticity: Changes in grey matter induced by training. NATURE Jan. 22, 2004; 427:311-2)

Coinciding with this recent research are growing demands from the aging US and world population who have become cognizant of the decline in cognitive health that often accompanies aging. Concerns such as loss of memory, decreased cognition, and mental illness associated with aging like Alzheimer's disease have fueled a growing market demand for products that help with maintaining and improving cognitive health.

DESCRIPTION

People interact with various forms of digital media on various computing devices on a daily basis. Interacting with different types of digital media requires the performance of various cognitive tasks, which stimulate different areas of the human brain. It may be useful to track an individual's usage of digital media across all the computing devices on which an individual interacts with digital media. The individual's interactions with digital media may be monitored by monitoring software built into the digital media, or residing on the computing devices that are used to access the digital media. The monitoring software may produce data representing various aspects of the individual's interaction with the digital media, e.g., how long they interacted with the digital media, what tasks they accomplished, etc.

The data produced by monitoring the individual's interaction with various forms of digital media across various computing devices may be aggregated and analyzed. The data may be analyzed in view of the cognitive tasks associated with the digital media interacted with by the user, as well as the areas of the human brain stimulated by those cognitive tasks. This may allow for the evaluation of the cognitive functions of the individual, e.g., overall cognitive health, improvements and declines in the performance of specific cognitive tasks, etc., and of patterns in the individual's usage of digital media, e.g., cognitive tasks the individual performs the most, cognitive tasks, and areas of the brain, the individual has neglected, etc. The individual may receive recommendations for other types of digital media to interact with based on the data, individualized plans for improving cognitive functions and stimulating certain brain areas, etc.

Some example embodiments include systems and methods that can be configured and executed to track human-digital media interactions. One exemplary embodiment may provide a system including a database that may store information regarding a user's activity history for various different cognitive tasks, and a computing device that may receive user behavior information indicating usage by a user of an interactive software program, the interactive software program associated with at least one of the cognitive tasks. The computing device may, in response to the receipt of user behavior information indicating usage by the user of the interactive software program, update the database information regarding the user's activity history for the at least one of the cognitive tasks.

Another exemplary embodiment may provide a system including a computing device that may execute an interactive software program configured to be used by a user and a storage device accessible to the computing device, the storage device storing data associating the interactive software program with at least one cognitive task. The computing device may, responsive to the user's use of the interactive software program, generate user behavior information for the user indicating the user's carrying out of the at least one of the plurality of cognitive tasks associated with the interactive software program in the data stored in the storage device.

Figure 1:
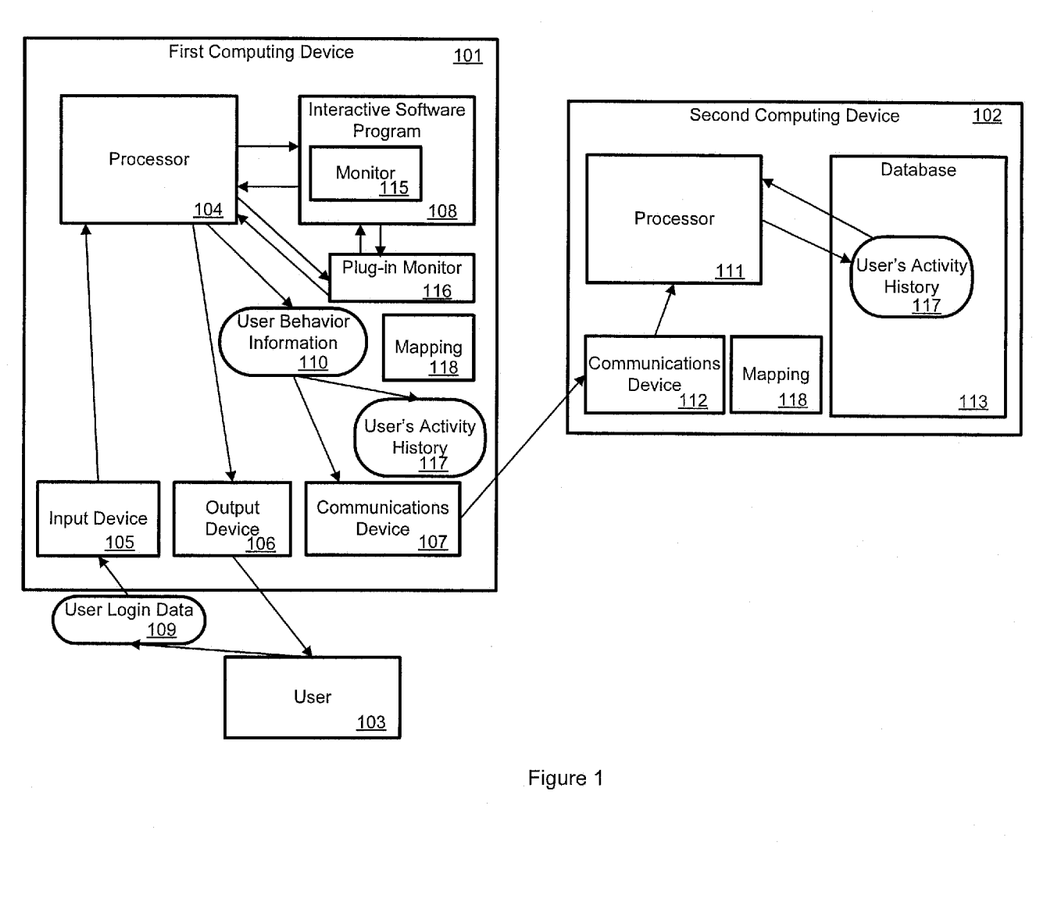
FIG. 1 depicts an exemplary system for tracking human-digital media interaction, according to one exemplary embodiment of the present invention.

FIG. 1 depicts an exemplary system for tracking human-digital media interaction. The exemplary system may include a first computing device 101 and a second computing device 102. A user 103 may interact with the first computing device 101. It will be appreciated that although two computing devices are illustrated in this example, the various features could be combined on a single device, e.g., using virtual machines, or spread over additional devices.

The first computing device 101 may be any suitable combination of hardware and software to allow interaction between the user 103 and an interactive software program. For example, the first computing device 101 may be a personal computer, a video game console, a mobile phone, a portable media player, a set-top box for a television, a mobile internet device, an e-book device, etc. The first computing device 101 may include a processor 104, an input device 105, an output device 106, and a communications device 107. A plug-in monitor 116, user's activity history 117, and a mapping 118, may be stored on the first computing device 101. An interactive software program 108 may be also be stored on the first computing device 101, or may reside on external media that can be accessed by the first computing device 101.

The processor 104 may be any general or special purpose microprocessor, depending on the nature and uses of the first computing device 101, suitable for executing, and allowing the user 103 to interact with, the interactive software program 108. For example, if the first computing device 101 is a personal computer, the processor 104 may be a general purpose processor from Intel®.

The input device 105 may be any suitable device connected to the first computing device 101 that allows the user 103 to input data into the first computing device 101. For example, the input device 105 may be a mouse, keyboard, keypad, trackball, touch-screen, haptic input device, microphone, video camera, drawing tablet, video game console controller, hard or soft key, gesture recognition hardware, etc. The first computing device 101 may make use of more than one input device 105, for example, a personal computer may have a mouse, a keyboard, a microphone and a video camera. The input device 105 may be connected to the first computing device 101 in any suitable manner, for example, using wired or wireless connections. The user 103 may use the input device 105 to login to the first computing device 101, using user login data 109. The user login data 109 may identify the individual user 103, for example, with a unique id, and may be any suitable data unique to the user 103, such as, for example, a password, a fingerprint, a voiceprint, a face-print, a hardware key, etc. On some computing devices, such as, for example, mobile phones, the identity of the user 103 may be automatically tied to the device, and may require no separate user login data 109. The user 103 may then use the input device 105 to control the operation of the first computing device 101, including interacting with the interactive software program 108.

The output device 106 may be any suitable device connected to the first computing device 101 that allows the user 103 to receive data output from the first computing device 101. For example, the output device 101 may be an LCD screen, a CRT monitor, a television, a speaker, a force feedback device, a haptic feedback device, a series of LEDs, etc. The first computing device 101 may make use of more than one output device 106, for example, a personal computer may have an LCD screen and a pair of speakers. The output device 106 may be connected to the first computing device 101 in any suitable manner, for example, using wired or wireless connections. The user 103 may receive data from the first computing device 101 through the output device 106, allowing the user 103 to interact with the first computer 101, including the interactive software program 108.

The communications device 107 may be any suitable device for allowing the first computing device 101 to send data to and receive data from any other computing device, for example, the second computing device 102. For example, the communications device 107 may be an 802.11x protocol based wireless (WiFi) card, an Ethernet device, a modem, a Bluetooth module, an IR link, etc. The first computing device 101 may make use of more than one communications device 107, for example, a personal computer may have a WiFi card a Bluetooth module. The communications device 107 may be connected to the first computing device 101 in any suitable manner, for example, using wired or wireless connections. The first computing device 101 may use the communications device 107 to transmit data, such as, for example, user behavior information 110, to the second computing device 102.

The interactive software program 108 may be any suitable program, executable by the processor 104, which allows interaction by the user 103. The interactive software program may be stored on the first computing device 101, or may reside on external media that can be read or accessed by the first computing device 101. For example, the interactive software program 108 may be a video game stored on a DVD and played on a video game console, a web-browser, a web-browser based game, a program installed on the hard drive of a personal computer including games and productivity applications, a text-messaging application or calling functionality of a mobile phone, a book reading application on an e-book, etc. The user 103 may interact with the interactive software 108 on the first computing device 101 using the input device 104. As a result of the interaction between the user 103 and the interactive software program 108, the user behavior information 110 may be generated for the user 103.

The user behavior information 110 may be data generated by the interaction between the user 103 and the interactive software program 108. This data may include, for example: how long the user 103 used the interactive software program 108, how much of that time the user 103 was actually interacting with the interactive software program 103, e.g., actively inputting or receiving data, and how much of the time the user 103 was interacting with distinct sections or tasks within the interactive software program 103; a score achieved by the user 103; a task accomplished by the user 103; a task not accomplished by the user 103; an amount of time taken by the user 103 to perform a task; a speed of input by the user 103, e.g. typing speed; an accuracy of input by the user 103, e.g. number of misspellings or errant mouse clicks; a reaction time of the user 103 to output from the interactive software program 103, e.g. in a first-person shooter video game, the amount of time it takes for a user to react to incoming fire by firing back or hiding; etc. Some interactions with the interactive software program 108 may be all or mostly passive, such as, for example, reading a book on an e-book device where the user 103 only interacts with the e-book to turn the page. Data for the user behavior information 110 may be inferred from combinations of passivity and activity for passive interactions, e.g. time spent reading a book on an e-book device may be inferred from the amount of time the book is loaded on the e-book and the frequency of page turning by the user 103.

Figure 2:
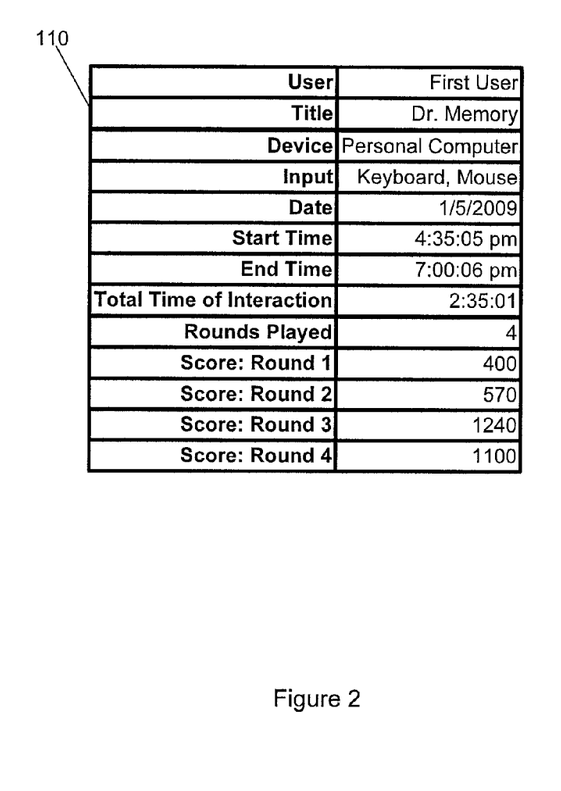
FIG. 2 depicts an exemplary record storing user behavior information, according to one exemplary embodiment of the present invention.

FIG. 2 depicts an exemplary record storing user behavior information. The exemplary user behavior information 110 may indicate that on Jan. 1, 2009, the user 103 interacted with an interactive software program 108 entitled Dr. Memory. The user 103 used a personal computer with a keyboard and a mouse, and interacted with Dr. Memory for a total of 2 hours, 35 minutes and 1 second. The user 103 completed 4 rounds of Dr. Memory, with scores of 400, 570, 1240, and 1100.

The interactive software program 108 may include a monitor 115. The monitor 115 may be a process in the interactive software program 108 that may monitor the interaction between the user 103 and the interactive software program 108 in order to generate the user behavior information 110. For example, if the interactive software program 108 is a video game on a video game console, the monitor 115 may run on the processor 104 along with video game and may track various statistics associated with the video game, such as, for example, time played, score achieved, tasks accomplished, etc.

The interactive software program 108 may, in some cases, not include the monitor 115. When the interactive software program 108 does not include the monitor 115, a plug-in monitor 116 may be used to provide the features of the monitor 116. The plug-in monitor 116 may be a software plug-in, or specialized hardware device, residing on the first computing device 101. When the user 103 begins interacting with an interactive software program 108 that does not have the monitor 115, the plug-in monitor 116 may be activated by the processor 104 and used to generate the user behavior information 110. For example, if the user 103 is playing a Flash game in a web-browser, and neither the Flash game nor the web-browser include the monitor 115 because the respective developers did not anticipate their program being used to generate the user behavior information 110, the plug-in monitor 116 may be used to generate the user behavior information 110 from the interaction between the user 103 and the Flash game. The plug-in monitor 116 may also reside on a computing device separate from the first computing device 101, such as, for example, in a cloud computing environment. The monitor 115 and plug-in monitor 116 may also be used in combination in some instances. For example, the monitor 115 may gather some data that can be used as the user behavior information 110, and some data that is extraneous, for example, hardware and software monitoring e.g. RAM used, page faults, CPU utilization, etc. The plug-in monitor 116 may receive all the data produced by the monitor 115, and sort out the data for the user behavior information 110 from the extraneous data.

The user's activity history 117 may be an aggregation of user behavior information 110 for the user 103, and may be stored on the first computing device 101. Alternatively, the raw user behavior information 110 may be stored and processed at a later time, although this may be more resource intensive. For every interactive software program 108 interacted with by the user 103, separate user behavior information 110 may be generated and stored in the user's activity history 117. If the user 103 has interacted with an interactive software program 108 on a computing device other than the first computing device 101, the user behavior information 110 for those interactions may also be stored in the user's activity history 117 on the first computing device 101 if the first computing device 101 receives, or can access, the user behavior information 110 from the other computing device. The user's activity history 117 may include other information along with the user behavior information 110, such as, for example, the identity of the interactive software program 108 responsible for generating each user behavior information 110, information about the interactive software program 108 taken from the mapping 118, and data that results from the processing and analysis of all or parts of the user behavior information 110.

Figure 3:
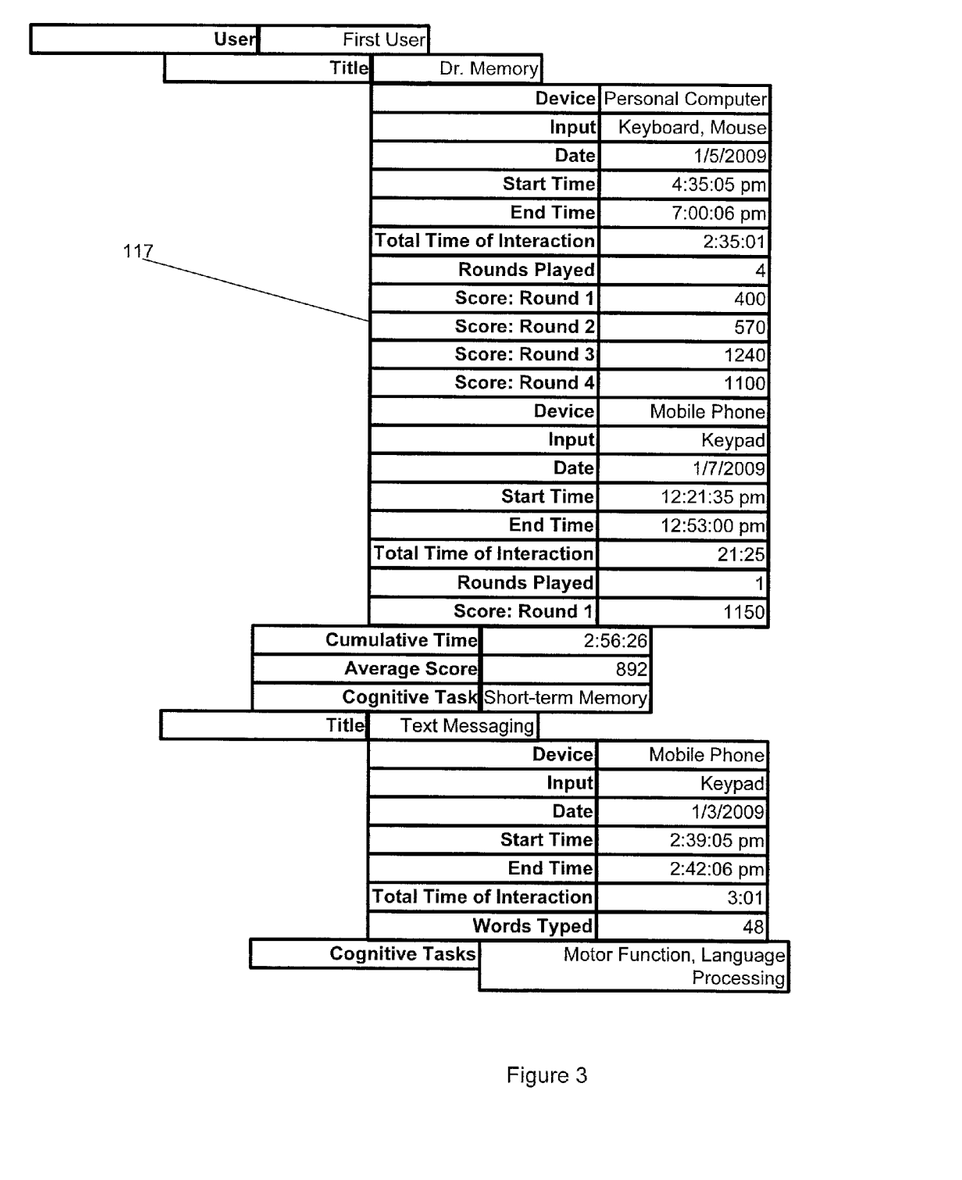
FIG. 3 depicts an exemplary record storing the user's activity history, according to one exemplary embodiment of the present invention.

FIG. 3 depicts an exemplary record storing the user's activity history. The exemplary user's activity history 117 may include the data from the user behavior information 110, as well as other user behavior information. The user 103 interacted with the interactive software program 108 Dr. Memory as indicated by the user behavior information 110, and again on Jan. 7, 2009. On Jan. 7, 2009 the user 103 interacted with Dr. Memory using a keypad on a mobile phone. The user 103 interacted with Dr. Memory for 21 minutes and 25 seconds, completed one round of play, and scored 1150. The exemplary user's activity history 117 includes a cumulative total time played for the user 103 for Dr. Memory of 2 hours, 56 minutes and 26 seconds, with an average score 892. The exemplary user's activity history 117 indicates that Dr. Memory may be associated with the cognitive task of short-term memory.

Also in the exemplary user's activity history 117, the user 103 used a text messaging application on a mobile phone on Jan. 3, 2009. The user 103 typed 48 words in 3 minutes and 1 second. The text messaging application may be associated with the motor function and language processing cognitive tasks.

The mapping 118 may be data stored on the first computing device 101 that may map interactive software programs, such as the interactive software program 108, to cognitive tasks performed through interaction with the interactive software programs, and may further map the cognitive tasks to the areas of the human brain stimulated during the performance of the cognitive tasks. Cognitive tasks may include, for example, short-term memory, long-term memory, attention, motor function, visual search, computation, speed of processing, verbal memory, task-switching, decision making, inhibitory control, and visual search, etc.

Figure 4:
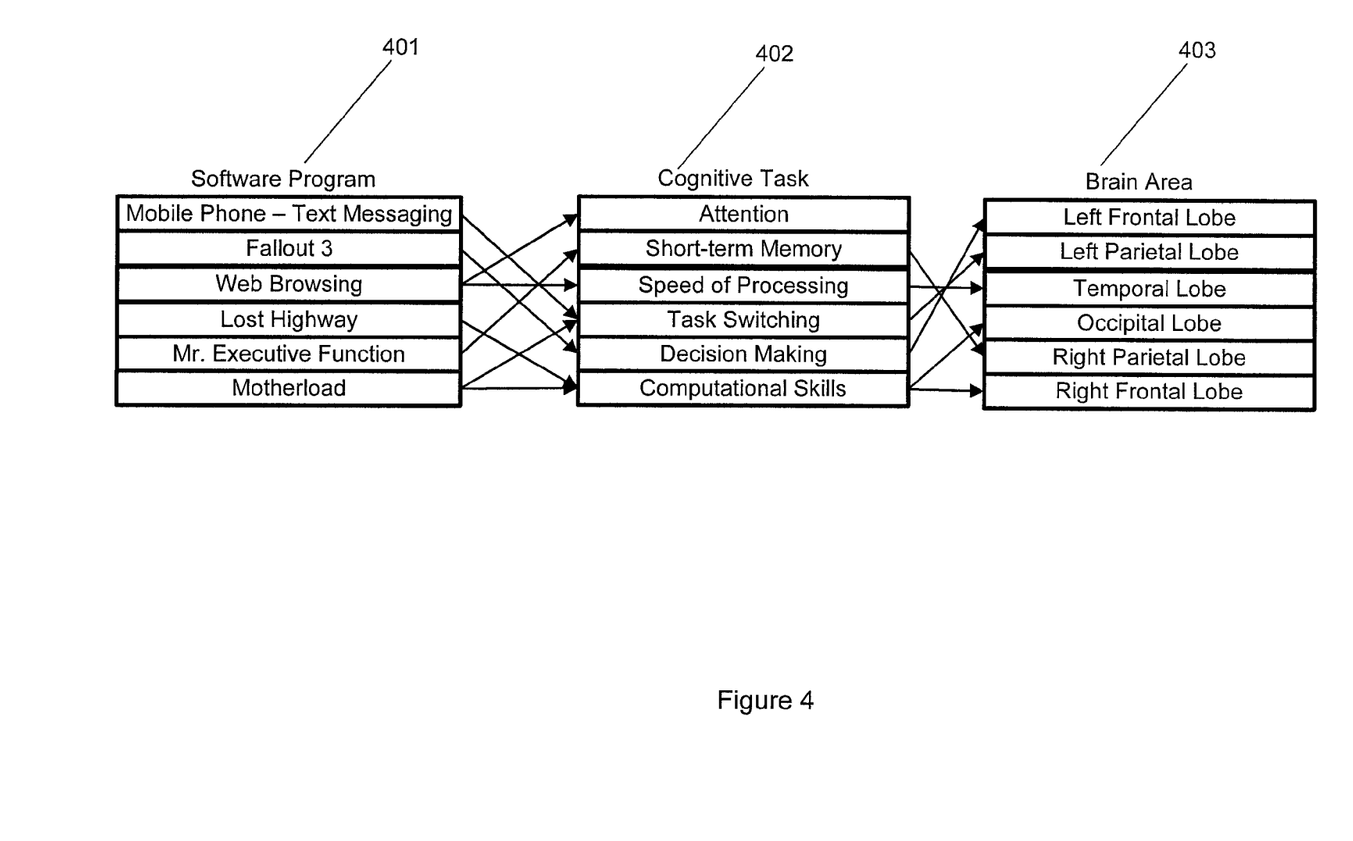
FIG. 4 depicts an exemplary representation of an interactive software program—cognitive task—brain area mapping, according to one exemplary embodiment of the present invention.

FIG. 4 depicts an exemplary representation of an interactive software program—cognitive task—brain area mapping. The representation of the mapping 118 may include a software program column 401, a cognitive task column 402, and a brain area column 403. The arrows in the representation may represent the mapping of items from one of the columns to items in the other columns, creating associations. For example, the arrow between "Lost Highway" in the software program column 401 and "Computational Skills" in the cognitive task column 402 may indicate that interacting with the interactive software program 108 "Lost Highway" requires the user to perform cognitive tasks involving computation. The arrow between "Computational Skills" in the cognitive task column 402 and "Right Frontal Lobe" in the brain area column 403 may indicate that performing cognitive tasks involving computation may stimulate the right frontal lobe of the human brain. Any interactive software program 108 may be mapped to any number of cognitive tasks, and any cognitive task may be mapped to any number of brain areas. Specific sections or parts of the interactive software program 108 may also be mapped to different cognitive tasks. For example, a video game may include sections of play that map to cognitive tasks for short-term memory and other sections that map to motor functions and reflexes. The mapping 118 may also include weights between interactive software programs 108, cognitive tasks, and areas of the brain. For example, an interactive software program 108 may require performance of both short-term memory and motor function cognitive tasks, but may place more emphasis on short-term memory, resulting in a heavier weight in the mapping 118 for the connection between the interactive software program 108 and the short-term memory cognitive task. Further, different cognitive tasks may be mapped to specific tasks within the interactive software program 108, instead of to the interactive software program 108 as a whole.

Based on the exemplary representation of the mapping 118 depicted in FIG. 4, if the user's activity history 117 shows that the user 103 has interacted with the interactive software program 108 "Lost Highway", it may be inferred that the user has performed cognitive tasks involving computation, and that these tasks have stimulated the right frontal lobe of the brain of the user 103.

The mapping 118 may be created by, for example, human analysis of various interactive software programs 108 for cognitive tasks. Automated tools may also be used to perform analysis of the interactive software programs 108, to create, or assist in the creation of, the mapping 118. The mapping 118 may also be based on data relating cognitive tasks to areas of the brain stimulated by performance of the cognitive tasks gathered using functional magnetic resonance imaging (fMRI), electroencephalography (EEG), positron emission tomography (PET), Magnetoencephalography (MEG), Event Related Optical Signal (EROS), near infrared spectroscopic imaging (NIRSI), event-related potential (ERP), Single Photon Emission Computed Tomography (SPECT), or Computed Tomography (CT).

The second computing device 102 may be any suitable combination of hardware and software to allow for the storage and analysis of the user's activity history 114. For example, the second computing device 102 may be a personal computer, a database server or server cluster, a computer on a distributed computing network, a suitable video game console or mobile computing device, etc. The second computing device 102 may include a processor 111, a communications device 112, and a database 113. The mapping 118, may be stored on the second computing device 102, or may reside on external media that can be read by the second computing device 102. The second computing device 102 may be, for example, a server, and the first computing device 101 may be a client.

The processor 111 and the communications device 112 may be similar to the processor 104 and the communications device 107. The database 113 may be any suitable combination of hardware and software, e.g., hard drives and database software, for the storing and accessing the user's activity history 117 for multiple users. The second computing device 102 may receive the user behavior information 110, including the identity of the user 103, from other computing devices, for example, the first computing device 101, through the communications device 112. The user behavior information 110 may be stored in the database 113 as part of the user's activity history 117 for the user 103, as described above.

Figure 5:
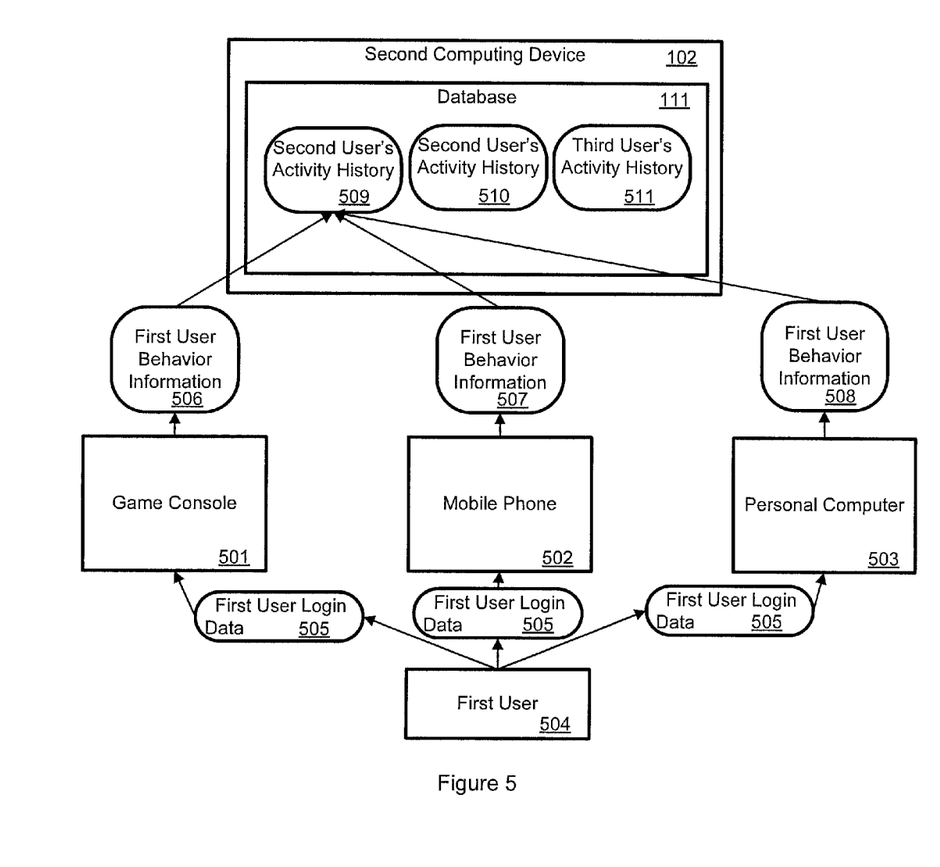
FIG. 5 depicts an exemplary system for tracking human-digital media interaction across multiple computing devices, according to one exemplary embodiment of the present invention.

FIG. 5 depicts an exemplary system for tracking human-digital media interaction across multiple computing devices. A first user 504 may login, at various times, to a video game console 501, a mobile phone 502, and a personal computer 503, using the first user login 505. The first user 504 may interact with interactive software programs 108 on the video game console 501, the mobile phone 502, and the personal computer 503. The interaction between the first user 502 and the interactive software program 108 on the video game console 501 may generate first user behavior information 506, on the mobile phone 502 may generate first user behavior information 507, and on the personal computer 503 may generate first user behavior information 508. The first user behavior information 506, 507, and 508 may be stored locally on the computing devices, and may also be transmitted to the second computing device 102. The second computing device 102 may store the first user behavior information 506, 507, and 508 in the database 113 as part of the first user's activity history 509, separate from the second user's activity history 510 and the third user's activity history 511. In this way, the interactions of the first user 504 with various interactive software programs 108 on various computing devices may be tracked, as all of the behavior information generated for the user 504 may be stored centrally.

In alternative embodiments, the first user's activity history 509 may be stored on any of the computing devices used the by the use 504, in place of or in addition to being stored on the second computing device 102. For example, the first user's activity history 509 may be stored on the personal computer 503, which may receive first user behavior information from other computing devices used by the user 503. The first user's activity history 509 may also, with suitable software and hardware, be stored in a distributed manner across multiple computing devices.

Figure 6:
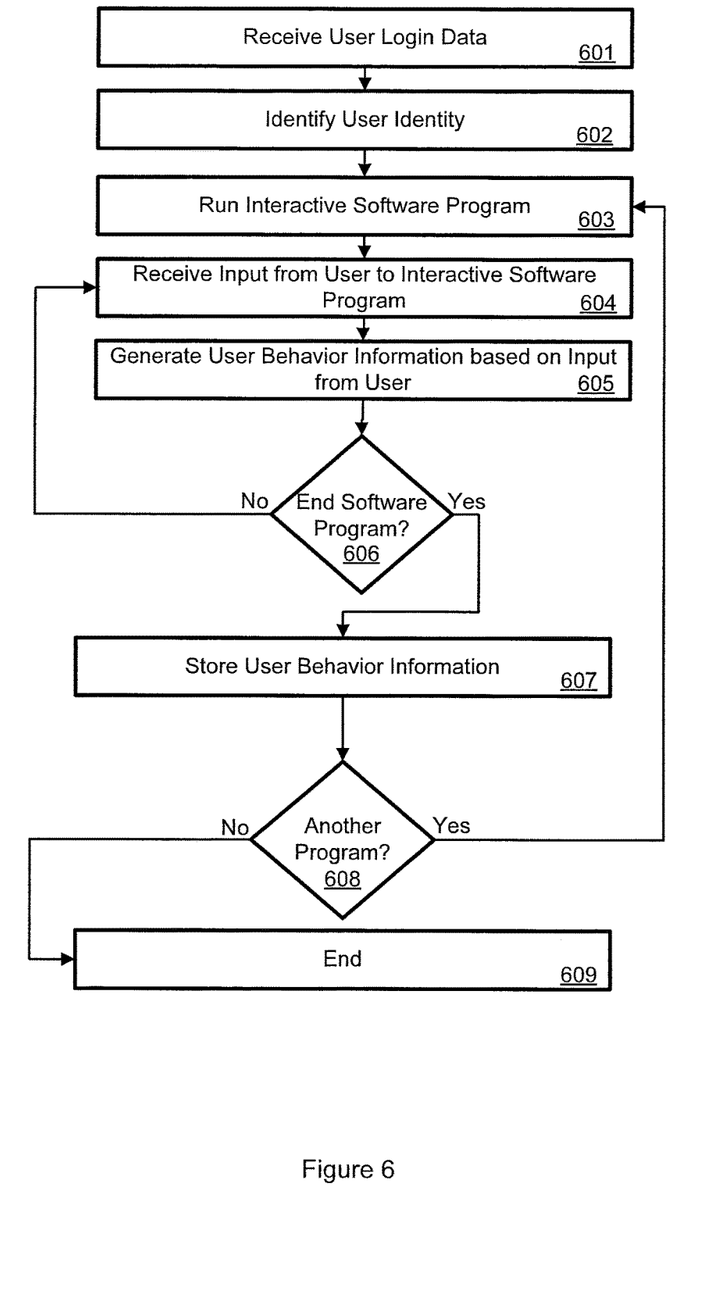
FIG. 6 is a flowchart depicting an example procedure for tracking human-digital media interaction, according to one exemplary embodiment of the present invention.

FIG. 6 depicts an exemplary flowchart for tracking human-digital media interaction. In block 601, a computing device may receive user login data from a user. For example, as depicted in FIG. 1, the first computing device 101 may receive the user login data 109 from the user 103.

In block 602, the user login data received in block 601 may be used to identify the user. Every user may need to be identified uniquely, to allow for the segregation of use behavior information for different users who use the same computing devices and interact with the same interactive software programs. For example, as depicted in FIG. 5, the first user login data 505 may be used to distinguish the first user 504 from any other users of the video game console 501, mobile phone 502, and personal computer 503, so that any user behavior information 110 for the first user 504 may be stored in the first user's activity history 509, separate from the second user's activity history 510 and the third user's activity history 511.

In block 603, an interactive software program may be run. For example, if the user 103 has logged in to the first computing device 101, the processor 104 may run the interactive software program 108 at the request of the user 103.

In block 604, the user may interact with the interactive software program run in block 603, and input may be received for the interactive software program from the user. The nature of the input received may depend on the type of computing device logged into by the user, the input devices connected to the computing device, and the nature of the interactive software program. For example, if the first computing device 101 is a personal computer and the interactive software program 108 is a Flash game played in a web browser, the user 103 may interact with the Flash game using a mouse and keyboard. As another example, if the first computing device 101 is a mobile phone and the interactive software program 108 is a text messaging application, the user 103 may interact with the text messaging application using a keypad on the mobile phone.

In block 605, interactions between the user and the interactive software program from block 604 may be used to generate user behavior information. For example, the monitor 115 may run on the processor 104 along with the interactive software program 108, and may monitor the interactions between the user 103 and the interactive software program 108. The interactions may be used to generate the user behavior information 110.

In block 606, the interactive software program may be ended. If the interactive software program is ended, flow proceeds block 607. Otherwise, flow proceeds back to block 604, as the user may continue to interact with the interactive software program.

In block 607, the user behavior information generated during block 605 may be stored. The user behavior information may be stored locally, remotely, or any suitable combination thereof, and may be aggregated with any previously stored user behavior information for the user in the user's activity history. For example, the user behavior information 110 may be stored on the first computing device 101 and/or transmitted to the second computing device 102 for storage. Storage of the user's activity history may be done in any suitable manner, including distributing the user's activity history across different storage media on the same or different computing devices, for example, across multiple hard drives in a RAID server, or multiple computing devices in a cloud storage system.

In an alternative embodiment, block 607 may run concurrently with block 605. Instead of waiting to store the user behavior information until after the interactive software program has ended in block 606, the user behavior information may be stored after generation in block 605.

In block 608, if the user runs another interactive software program on the computing device, flow proceeds back to block 603. Otherwise flow proceeds to block 609 and ends. The user 103, after finishing with the interactive software program 108, may choose to run a different interactive software program on the computing device 101. For example, if the user 103 finishes using a text messaging application on a mobile phone after sending a text message, the user 103 may then use the voice functionality of the mobile phone to make a phone call.

On some computing devices, it may be possible to run more than one interactive software program 108 at a time, allowing the user 103 to interact with a second interactive software program 108 without ending a first interactive software program 108. For example, on a personal computer running a modern operating system, a user 103 may have many interactive software programs 108 running simultaneously. User behavior information 110 may be generated for all interactive software programs 108 running simultaneously, so long as every piece of information in the user behavior information 110 is associated with the correct interactive software program 108.

Figure 7:
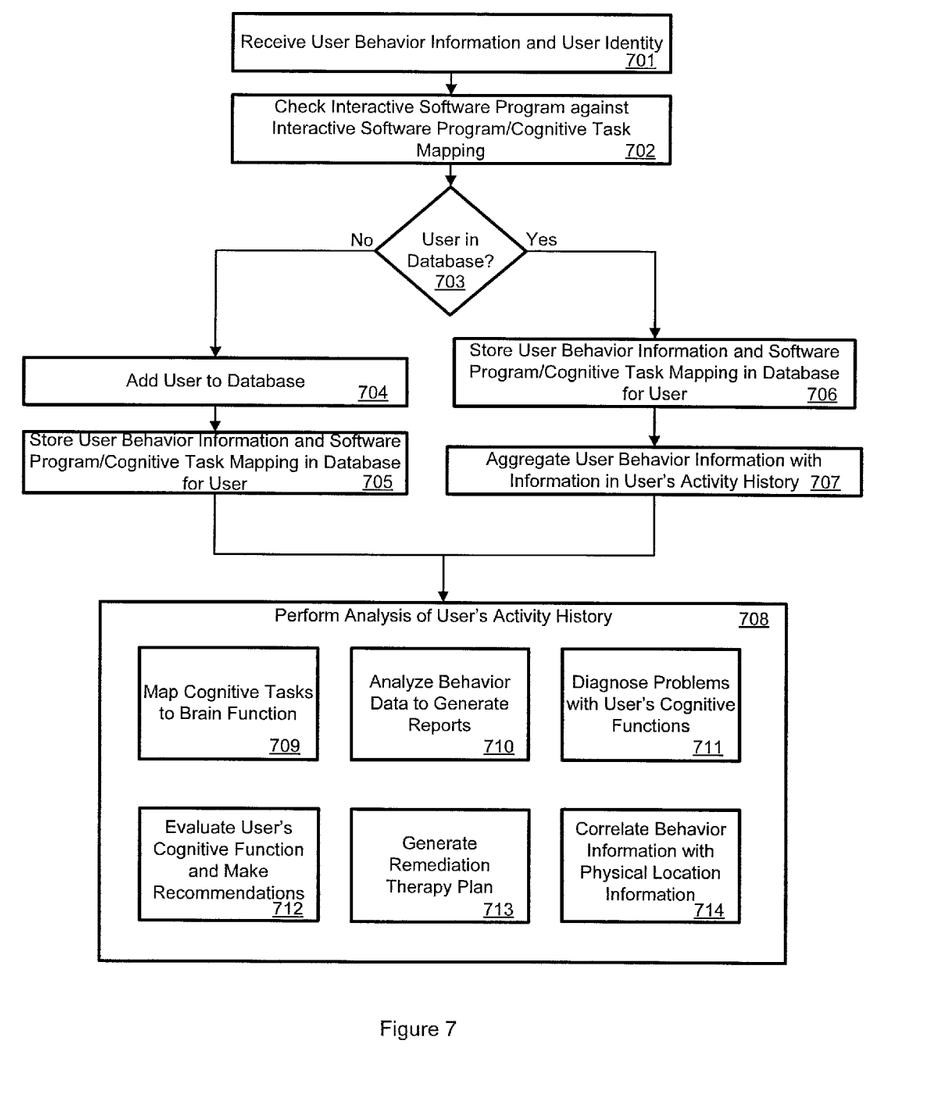
FIG. 7 is a flowchart depicting an example procedure for storing and analyzing user behavior information generated from tracking human-digital media interaction, according to one exemplary embodiment of the present invention.

After the user behavior information 110 has been generated, the user behavior information 110 may undergo processing while, or after, being stored. FIG. 7 depicts an exemplary flowchart for storing and analyzing behavior information generated from tracking human-digital media interaction.

In block 701, the user behavior information and user identity may be received by a computing device. The user identity may be any form of digital identification, for example, a user name, a user id number, etc, that can be used to identify a unique user based on the user login data. For example, the second computing device 102 may receive the user behavior information 110 and user identity for the user 103 from the first computing device 101. As another example, if the user behavior information 110 is being stored on the first computing device 101, where the user behavior information 110 was generated, then the appropriate program for processing and storing the user behavior information 110 may receive the user behavior information 110 and the user identity of the user 103.

In block 702, the interactive software program for which the user behavior information was generated may be checked against an interactive software program-cognitive task mapping. For example, as described previously, the interactive software program 108 may be checked against the mapping 118, to determine which cognitive tasks the software program 108 is associated with. If the interactive software program 108 is associated with more than one cognitive task, the user behavior information 110 may also be checked to determine which of the cognitive tasks the user 103 may have actually preformed while interacting with the interactive software program 108.

In block 703, if the user is already in the database, flow proceeds to block 706. Otherwise flow proceeds to block 704.

In block 704, the user may be added to the database, so that the user behavior information may be stored in the database. For example, if the user 103 is not in the database 113 when the second computing device 102 receives the user behavior information 110, the user 103 may be added to the database 113.

In block 705, the user behavior information and additional data for the user just added to the database may be stored in the database in the user's activity history. Additional data may include identification of the interactive software program, as well as results of checking the interactive software program against the mapping. For example, if the user 103 has just been added to the database 113, the user behavior information 110 may be stored in the database 113 as the user's activity history 117.

In block 706, the user is already in the database, so the user behavior information and additional information may be stored in the database, in the user's activity history. For example, if the user 103 is in the database 113, the user behavior information 110 may be stored in the user's activity history 117.

In block 707, the user behavior information may be aggregated with the user behavior information already stored for the user in the database. Aggregating user behavior information may involve, for example, updating cumulative totals for the same interactive software program, updating cumulative totals for the same cognitive task, etc. For example, the user behavior information 110 may be aggregated with any data already in the user's activity history 117 in the database 113.

In block 708, the user's activity history may be analyzed. Analysis may occur on the entirety or any subset of the user's activity history. Blocks 709-714 are examples of the types of analysis that may be performed on the user's activity history.

In block 709, the cognitive tasks present in the user's activity history may be mapped to the areas of the human brain stimulated. For example, the mapping 118 may be used to determine which areas of their brain the user 103 has spent the most or least time stimulating, based on the cognitive tasks the user's activity history 117 indicates the user has performed, and the amount of the time the user 103 performed those cognitive tasks, while interacting with interactive software programs 108. If the user 103 has spent 20 hours interacting with interactive software programs 108 that involve short-term memory related cognitive tasks, and only 4 hours interacting with interactive software programs 108 that involve motor function related cognitive tasks, analysis based on the mapping 118 may indicate that the user 103 has spent the most time stimulating the short-term memory related area of the brain, and the least time stimulating the motor function of the brain. This may provide the user 103 with information that can be used to balance the user's 103 use of different types of interactive software programs 108, or to suggest or report training and interactive software programs 108 for the user 103 to interact with to achieve goals based on a profile of the user 103.

In block 710, the user's activity history may be analyzed to generate reports. The reports may be in the form of text, charts, graphs, animations, and/or illustrations. The reports may include data related to any aspect of the user's activity history. For example, the reports may only indicate how much time the user 103 has spent on different cognitive tasks, or stimulating different areas of the user's 103 brain. As another example, the report may track the user's 103 level of performance of specific cognitive tasks over a period of time, showing how the level of the user's 103 performance has varied based on the passage of time, or in relation to the user's 103 level of performance of other cognitive tasks, usage of interactive software programs 108, etc.

In block 711, the user's activity history may be used to diagnose problems with the user's cognitive functions. For example, if the user's activity history 117 shows that the user's 103 level of performance on cognitive tasks related to short-term memory has consistently decreased over a period of time, the user 103 may be diagnosed with a condition affecting short-term memory. Diagnoses may make use of any type of data from the user's activity history, and may also make use of any known data about the user, for example, age, previous health problems, etc.

In block 712, the user's activity history may be used to evaluate the user's cognitive functions, and to make recommendations of interactive software programs for the user to use. For example, the level of performance of the user 103 at various cognitive tasks may be determined from the user's activity history 117, and may be used to recommend to the user 103 interactive software programs 108 that will help the user 103 improve at cognitive tasks at which they show deficiencies, perform cognitive tasks that the user 103 has spent less time on, sharpen the user's 103 ability to perform specific cognitive tasks that the user 103 is already good at but wishes to be better at, etc. For example, if the user 103 has spent 20 hours interacting with interactive software programs 108 that involve short-term memory related cognitive tasks, and only 4 hours interacting with interactive software programs 108 that involve motor function related cognitive tasks, or the user 103 has shown a high level of short-term memory performance but a low-level of motor function performance, the usage of interactive software programs 108 that involve motor function related cognitive tasks, or use other cognitive tasks to stimulate the areas of the brain responsible for motor function, may be recommend to the user 103.

In block 713, the user's activity history may be used to generate a plan for remediation therapy for the user. For example, if the user 103 is known to have a particular condition affecting their cognitive function, e.g., a recent stroke, the user's activity history 117 may be used to generate plan for remediation therapy to improve the areas cognitive function and related areas of the brain affected by the user's 103 condition. The plan may include recommendations of interactive software programs 108 the user 103 should interact with, a schedule providing for when and how long the user 103 should interact with certain interactive software programs 108, goals or checkpoints for the user's 103 level of performance at certain cognitive functions, etc.

In block 714, the user's activity history may be correlated with physical location information for the user. Physical location information may include information tracking the user's movements throughout the physical world, such as, for example, GPS data, cell-phone location tracking data, RFID tag data, etc. Correlating the user's activity history to the physical location information may allow for analysis of how the user interacts with computing devices and interactive software programs during the course of the user's daily life, and how time of day and location affect the user's cognitive functions. For example, physical location data may allow for analysis of the user's activity history 117 to determine that the user's 103 motor function is impaired if the user 103 is talking on a mobile phone while driving a car.

Another example of analysis that may be performed on the user's activity history includes correlating the user's activity history with data from medical devices, such as, for example, fMRI data for the user. An fMRI may be used to monitor the user's 103 brain function while the user 103 performs a cognitive task, and the data produced by the fMRI may be correlated with data for the cognitive task from the user's activity history 117. The correlation may be used, for example, to gage the overall effect of the user's 103 use of interactive software programs 108 on the user's 103 brains ability to carry out the cognitive task.

Figure 8:
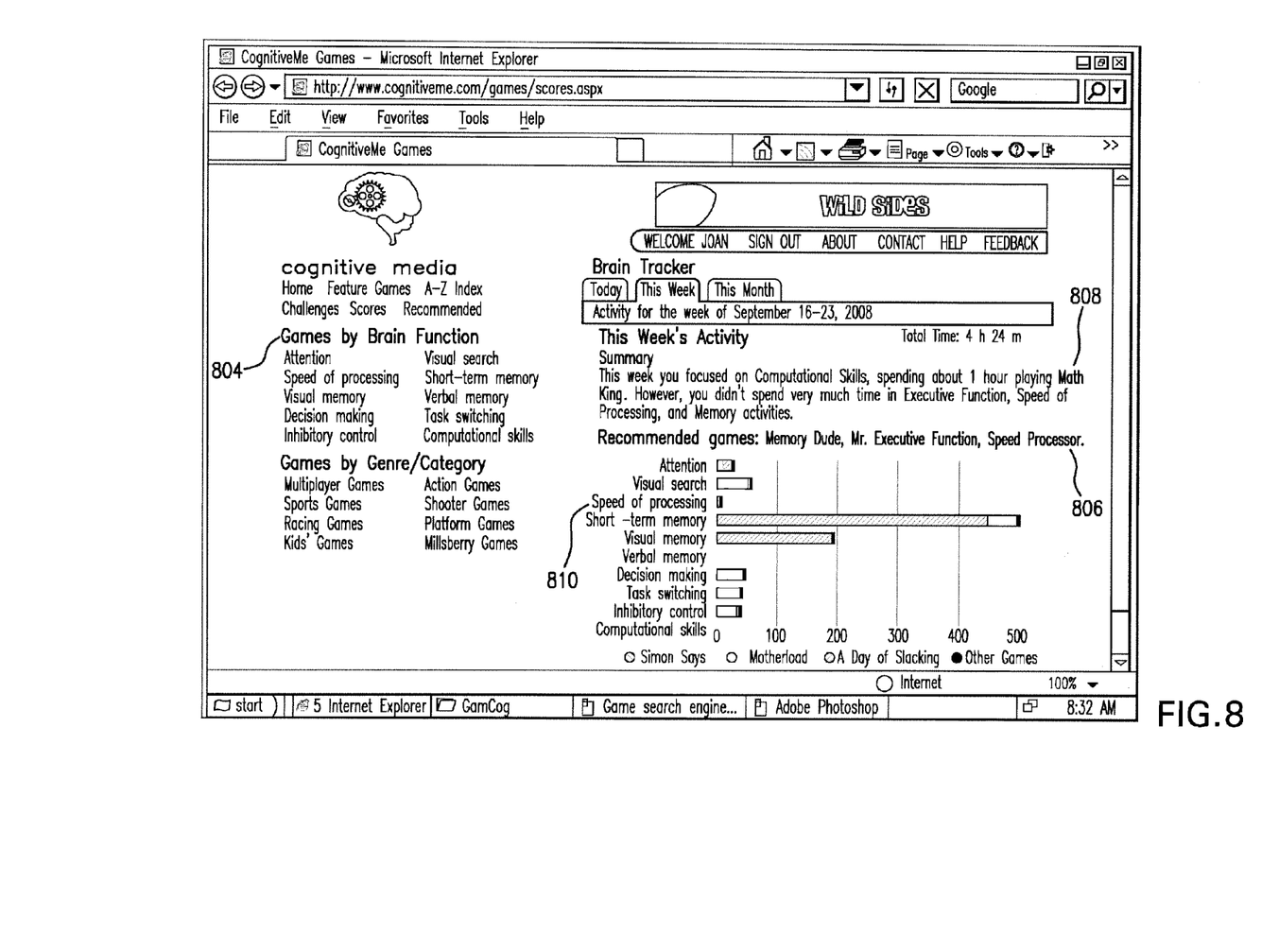
FIG. 8 depicts an exemplary screenshot from an exemplary system for viewing analyses and recommendations based on a user's activity history, according to one exemplary embodiment of the present invention.

FIG. 8 depicts an exemplary screenshot of a screen for viewing analyses and recommendations based on the user's activity history. The exemplary screenshot depicts a quantitative analysis 810 of a user's activity history. According to the qualitative summary 808 of the quantitative analysis 810, the user has spent more time during the previous week focusing on computation related cognitive tasks. The set of recommendations 806, based on the quantitative analysis 810, recommend that the user use interactive software programs focused on memory, speed of processing, and executive function cognitive tasks. Also depicted are exemplary cognitive tasks categories 804.

In alternative embodiments, the user behavior information 110 may be analyzed before being stored with user's activity history 117. This analysis may be done in the same manner as the analysis of the user's activity history 117, though it may produce less comprehensive results as it may involve analyzing less data than is available in the user's activity history 117.

With reference to FIG. 1, the user 103 may use a variety of computing devices. Examples of computing devices include, without limitation, computer systems, personal digital assistants, notebook computers, and/or telephones (of either wireline or wireless variety). Examples of communication media that can be employed include, without limitation, wireless data networks, wireline networks, and/or a variety of networked media.

As used herein, a "computer" or "computer system" may be, for example and without limitation, either alone or in combination, a personal computer (PC), server-based computer, main frame, server, microcomputer, minicomputer, laptop, personal data assistant (PDA), cellular phone, pager, processor, including wireless and/or wireline varieties thereof, and/or any other computerized device capable of configuration for receiving, storing and/or processing data for standalone application and/or over a networked medium or media.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system. Memory may also include any means for storing software or other instructions including, for example and without limitation, a hard disk, an optical disk, floppy disk, DVD, compact disc, memory stick, ROM (read only memory), RAM (random access memory), PROM (programmable ROM), EEPROM (extended erasable PROM), and/or other like computer-readable media.

In general, computer-readable media may include any medium capable of being a carrier for an electronic signal representative of data stored, communicated or processed in accordance with embodiments of the present invention. Where applicable, method steps described herein may be embodied or executed as instructions stored on a computer-readable medium or media.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these and other elements may be desirable. However, because such elements are well known in the art, and because they do not facilitate a better understanding of the present invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the present invention, a single component may be replaced by multiple components, and multiple components may be replaced by a single component, to provide an element or structure or to perform a given function or functions. Except where such substitution would not be operative to practice certain embodiments of the present invention, such substitution is considered within the scope of the present invention.

The examples presented herein are intended to illustrate potential and specific implementations of the present invention. It can be appreciated that the examples are intended primarily for purposes of illustration of the invention for those skilled in the art. The diagrams depicted herein are provided by way of example. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the following claims.

What is claimed is:

1. A system for cognitive training based on user-digital media interaction tracking, comprising:
   a plurality of computing devices having a plurality of commercially available third-party interactive digital media stored therein, said digital media including a video game and a web-browser, each of the plurality of computing devices including:
      a processor and a memory, the memory including:
         one or more of the plurality of digital media in the form of executable software programs;
         a user-digital media interaction monitor configured to plug-in as a monitoring extension to each of the digital media without modification of interactive content of said digital media, the user-digital media interaction monitor having executable instructions that configure the computing device to:
            identify a user identity for the user; and
            unobtrusively track the user-digital media interaction, which includes a speed and duration of active interaction of the user with each of the plurality of digital media;
   a computer server with a processor and a memory, the memory including:
      a database having a first predetermined weighted mapping between each of the plurality of digital media with one or more of a plurality of cognitive tasks, and a second predetermined weighted mapping between each of the plurality of cognitive tasks with one or more of a plurality of brain areas, wherein the plurality of cognitive tasks include at least two of memory, attention, motor function, visual search, decision making, inhibitory control, computation and speed of processing; and executable instructions that configure the computer server to:

perform an analysis that determines a duration of exercise of each of the plurality of cognitive tasks and brain areas for the user based on the first predetermined weighted mapping, the second predetermined weighted mapping and a daily, weekly or monthly history of the user-digital media interaction across the plurality of the computing devices; and determine a plan of cognitive exercise of one or more of the plurality of cognitive tasks and one or more of the plurality of brain areas for the user, the plan including a schedule with a recommended duration of user-digital media interaction with each of the plurality of digital media; and serve the plan to at least one of the computing devices;

wherein each of the computing devices are further configured to receive and display the plan.

2. The system of claim 1, wherein the memory of one of the computing devices further includes executable instructions that configure the one of the computing devices to perform a computing device specific analysis of a history of device specific user-digital media interaction on the one of the computing devices.

3. The system of claim 1, wherein the analysis further comprises at least one of: analyzing the user-digital media interaction to produce charts, graphs, illustrations, or animations, generating recommendations for the user of an additional executable interactive software program associated with an additional cognitive task, evaluating the user's cognitive functions, diagnosing a deficiency in the user's cognitive functions, generating a plan for remediation therapy to address a deficiency in the user's cognitive functions, and correlating the user-digital media interaction history with physical location data.

4. The system of claim 1, wherein the memory of one of the computing devices further includes a history of device specific user-digital media interaction on the one of the computing devices.

5. The system of claim 1, wherein the first and the second mappings are based on electroencephalography (EEG) data.

6. The system of claim 5, wherein the digital media further include a text messaging application, and the brain area includes at least one of left frontal lobe, left parietal lobe, temporal lobe, occipital lobe, right frontal lobe, and right parietal lobe.

7. The system of claim 1, wherein the digital media further include a text messaging application.

* * * * *